US006406463B1

(12) United States Patent
Brown

(10) Patent No.: US 6,406,463 B1
(45) Date of Patent: Jun. 18, 2002

(54) COVER FOR URINE COLLECTION CONTAINER

(76) Inventor: Chiquita B. Brown, 1027 Bourbon Pl., Memphis, TN (US) 38106-1504

( * ) Notice: Subject to any disclaimer, the term of this patent is extended or adjusted under 35 U.S.C. 154(b) by 0 days.

(21) Appl. No.: 09/624,153

(22) Filed: Jul. 24, 2000

(51) Int. Cl.[7] .................................................... A61F 5/44

(52) U.S. Cl. ......................... 604/349; 4/144.1; 4/144.2; 604/346

(58) Field of Search ................................ 604/346, 327, 604/544, 349, 319, 404; 215/11.6; D7/607, 625; 4/144.1, 144.2

(56) References Cited

U.S. PATENT DOCUMENTS 3,716,871 A * 2/1973 Borse ............................ 4/110
3,814,288 A * 6/1974 Westrich ..................... 222/129
D406,989 S * 3/1999 Rausch ......................... D7/624
D421,366 S * 3/2000 Mogil .......................... D7/625
D432,873 S * 10/2000 Fair ............................ D7/624
6,163,892 A * 12/2000 Abbato ....................... 4/144.1

* cited by examiner

*Primary Examiner*—John G. Weiss
*Assistant Examiner*—Jacqueline F Stephens
(74) *Attorney, Agent, or Firm*—Garvey, Smith, Nehrbass & Doody, LLC

(57) ABSTRACT

A urine collection container apparatus includes a vessel and a cover that is specially configured to envelope and remain connected to the vessel during use. The cover has a window that enables the level of fluid within the vessel to be checked even when the cover remains on the vessel.

14 Claims, 3 Drawing Sheets

COVER FOR URINE COLLECTION CONTAINER

CROSS-REFERENCE TO RELATED APPLICATIONS

Not applicable

STATEMENT REGARDING FEDERALLY SPONSORED RESEARCH OR DEVELOPMENT

Not applicable

REFERENCE TO A "MICROFICHE APPENDIX"

Not applicable

BACKGROUND OF THE INVENTION

1. Field of the Invention

The present invention relates to urine collection containers and protective covers therefor. More particularly, the present invention relates to an improved cover that removably attaches to a urine collection container, provides a snug fit with the container specifically over the bottom thereof so as to provide a stable base for the container in its upright condition and total enclosure of the bottom when it is in its prone position.

2. General Background of the Invention

Several patents have issued that disclose various urine collection containers. Examples of those patents are contained in the following table:

| Patent | Issue Date | Title |
|---|---|---|
| 3,727,244 | 04/17/73 | Dry Closet Urinal |
| 4,094,648 | 06/13/78 | Urine Specimen Container |
| 4,309,779 | 01/12/82 | Personal Urinal Device Useable by Males and Females |
| 4,901,375 | 02/20/90 | Male Urinal Appliance |
| 5,797,147 | 08/25/98 | Spill-Resistant Urinal |

Other patents have issued that relate to cover devices that can be used to protect, insulate or cover a container. Examples of those patents are found in the following table:

| Patent | Issue Date | Title |
|---|---|---|
| 4,526,280 | 07/02/85 | Bottle Cover |
| 5,680,944 | 10/28/97 | Insulated Outer Layer for a Thermal Bottle |
| 5,927,524 | 07/27/99 | Bottle Safety Blanket |

The numbers of individuals using urinal bottles is increasing for several reasons: an increase in the incidence of prostate problems and other urological disorders; an ever-increasing aged population with a greater propensity for longevity and the resultant age-associated disabilities; and the increased use of hand-held urinals by able-bodied men who find their use a convenience; i.e., policemen on stake-out who are unable to leave their vehicle and over the road professional drivers who are between scheduled stops or are otherwise schedule pressed. The sight of a partially full urinal bottle is disconcerting to users and those with whom they may come into contact. Completely removing the urinal from view by placing it into a cabinet or other receptacle subjects infirmed users to the problem of retrieval when the urinal is needed. Many users suffer from short-term memory loss and physical disabilities. Heretofore, there has not been a suitable cover which offers discretion for the user while simultaneously allowing for a visual inspection of contents or out-put measurements for the infirmed users in hospitals, nursing homes and those receiving home-bound care from home health providers. The vertical window in the preferred embodiment of my invention for health care use meets this shortcoming. Additionally, the inventive cover is one which is easily installed yet allows the bottle to sit upright in a stable mode when the bottle is not in use. Covers illustrated in the above patents, whether for urinal bottles or for bottles of other applications don't show or suggest the successful configuration of the present invention. In preferred alternative embodiments, the cover may be preferably of a lightweight cloth or similar non-woven synthetic material. Likewise, it is advantageous if the material is treated with an anti-bacterial agent and is water resistant.

BRIEF SUMMARY OF THE INVENTION

The present invention is directed to a cover for a urine collection container of the type utilized in hospitals, nursing homes and of the type sold in pharmacies and medical supply houses for use in at-home care by totally or partially bed-ridden patients, or by other individuals seeking the convenience of a portable urine collection container. The invention includes a vessel and a cover which is configured to snugly envelope the vessel during use. The cover may include a window disposed vertically over at least the mid and/or upper ranges of the vessel for observing the degree of fill in the container. The cover is adapted for ease of installation by including an elastic portion disposed at its upper extent which is approximately at the neck portion of the vessel when the cover is installed. The cover may be seamed vertically on one side, preferably adjacent the handle portion of the vessel, wherein the seam terminates in a vertical opening terminated at the top adjacent the elastic with a closure such as hook and loop fasteners, snaps, buttons or similar closeable fasteners.

BRIEF DESCRIPTION OF THE DRAWINGS

For a further understanding of the nature, objects, and advantages of the present invention, reference should be had to the following detailed description, read in conjunction with the following drawings, wherein like reference numerals denote like elements and wherein.

DETAILED DESCRIPTION OF THE INVENTION

Figure 2:
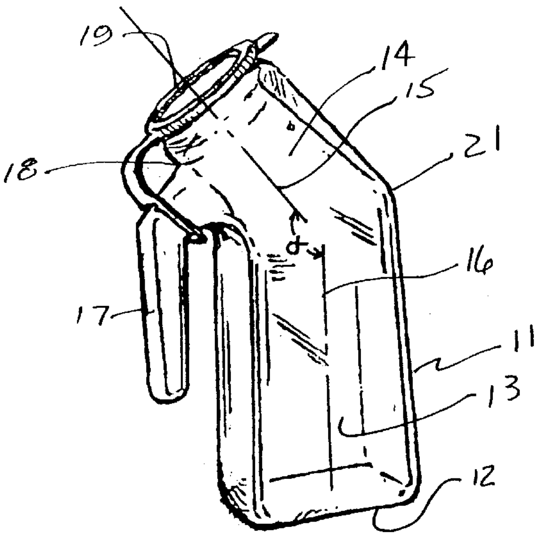
FIG. 2 is a partial, perspective view of the preferred embodiment of the apparatus of the present invention illustrating the receptacle portion thereof.
Figure 3:
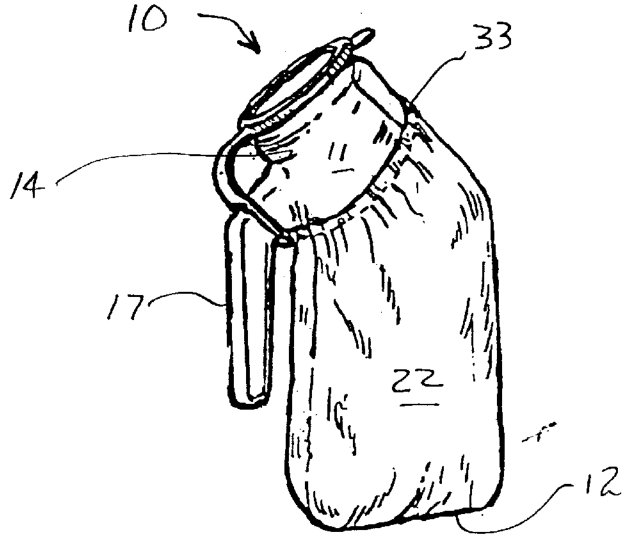
FIG. 3 is a partial, perspective view of the preferred embodiment of the apparatus of the present invention illustrating the cover disposed on the receptacle portion thereof.

FIG. 3 shows the preferred embodiment of the apparatus of the present invention designated generally by the numeral 10. Urine collection container apparatus 10 includes a vessel 11 (illustrated in FIG. 2) and an associated cover 22. In FIG. 2, the vessel 11 can provide a bottom 12, a plurality of side walls 13, a neck 14, handle 17 and cap 19. For purposes of reference, a pair of reference lines 15, 16 are shown in FIG. 2. The reference line 15 represents the central longitudinal axis of the lower portion of the vessel 11 below bend 21. The reference line 16 represents the central longitudinal axis of the neck 14 above bend 21. The reference lines 15 and 16 form an obtuse angle a of about 120–160 degrees. Handle 17 is connected to container neck 14 at joint 18 which can be an integral joint if the vessel is manufactured, for example, of glass or plastic.

Figure 4:
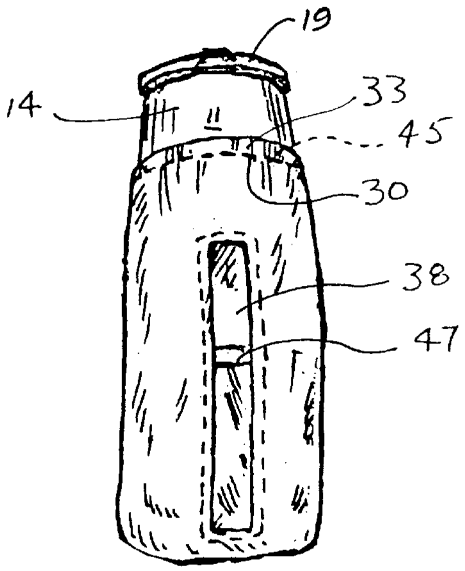
FIG. 4 is another perspective view of the preferred embodiment of the apparatus of the present invention.
Figure 5:
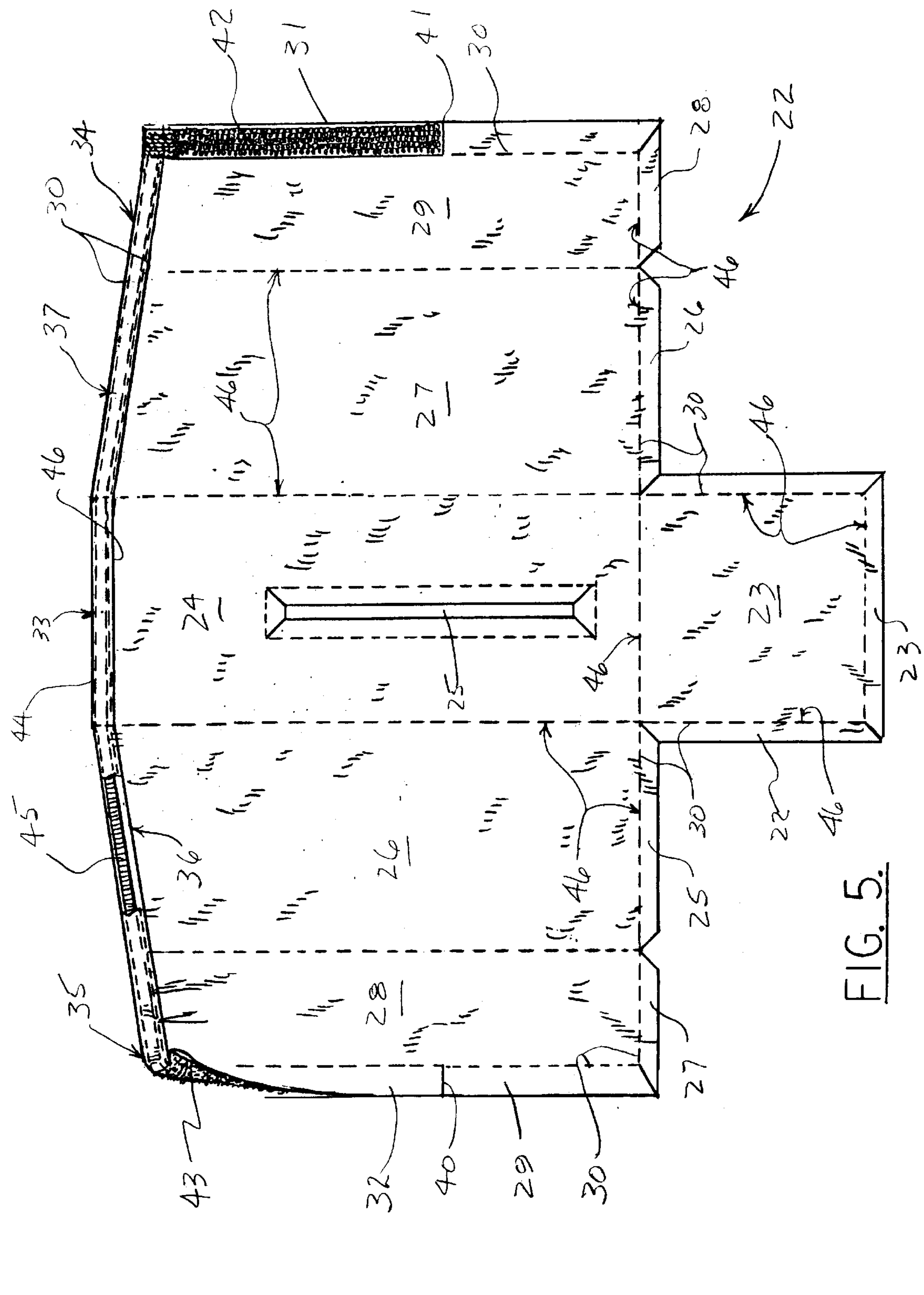
FIG. 5 is a partial plan view of the preferred embodiment of the apparatus of the present invention illustrating the cover in an expanded, unfolded position prior to assembly using stitching.

In FIGS. 1, 3, 4, and 5, cover 22 includes a plurality of panels that are preferably, however may be stitched together. In FIG. 5, the unsewn cover 22 includes bottom panel 23, large rear panel 24, side panels 26, 27 and front panels 28, 29. In the preferred embodiment illustrated the large rear panel 24 has a vertically extending window 25 that enables a nurse or medical personnel to place the apparatus 10 in the upright position on base 12 as illustrated in FIGS. 3 and 4 in order to check the fluid level by checking window 25. In FIG. 4, the fluid level is indicated by the numeral 47. Alternative embodiments of cover 22 may omit the window where the inclusion of such is unnecessary (where there is no need for a visual inspection or measurement of the contents) or adds undesirable over-all cost to cover 22. While the anticipated principal use of container 11 and cover are in the home or health care environment, urine containers may be also utilized for convenience, particularly by males, where an individual is precluded from leaving an area for a prolonged period of time, as is police officers on stake-out or over-the-road drivers.

Figure 1:
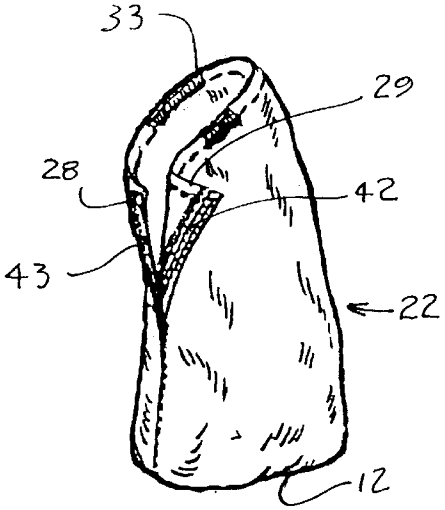
FIG. 1 is a partial, perspective view of the preferred embodiment of the apparatus of the present invention.

Stitching may be used to assemble cover 22 into the configuration of FIGS. 1, 3 and 4. In FIG. 5, stitching is indicated by the phantom lines 30. Also shown in phantom lines in FIG. 5 are various folds indicated by the numeral 46. For the front panels 28, 29, stitching is shown below reference lines 40, 41 and folds 46 are shown above the reference lines 40, 41. This is because there are provided connector panels 31, 32 above reference lines 40, 41 that enable the side panels 28, 29 to be separated, such as during removal or insertion of vessel 11. This partial separation of the panels 28, 29 is shown in FIG. 1. In the preferred embodiment, hook and loop connector panels can be used such as for example, a hook connector panel 42 and a loop connector panel 43 disposed on connector panes 31 and 32. Those skilled in the art will recognize that if cover 22 is made of a non-woven, synthetic material rather than such as a cotton or blend thereof, that the "stitching" process may an ultrasonic "welding" facilitating the manufacturing process. Alternatively, other suitable methods of fixing material at a seam may also be used including adhesives and the like. Likewise, those skilled in the art will recognize that connector means other than hook and loop fastener material, such as snaps, hooks and eyes, zippers, buttons and holes may be alternatively effective connectors.

An upper panel 44 is an elongated panel that extends across the upper edge of each of the panels 24, 26, 27, 28, 29, and in each of those regions is designated as peripheral panel 33, 37, 36, 35, 34, respectively. This upper panel 44 carries an elastic band 45 in between upper and lower stitched portions 30 as shown in FIG. 5. This upper panel 44 with elastic band 45 enables the cover 22 to tightly grip the neck 14 region of the vessel 11 as shown in FIGS. 3 and 4. It should also be understood that the peripheral panels 33, 37, 36, 35 and 34 in FIG. 5 describe a generally straight line and that the panel 33 is perpendicular to the vertical fold lines 46 of large rear panel 24 but panels 37, 36, 35 and 34 form an acute angle with the folds 46 forming the side lines of panels 28, 26, 27, and 29. Such a construction enables the cover 22 to extend upwardly toward the cap 19 of vessel 11 thus covering a large portion of neck 14. Neck 14 can be conically shaped or tapered as shown in FIG. 4. In such a situation, the band 45 of upper panel 44 helps prevent slippage of the entire cover 22 downwardly during use.

Figure 6:
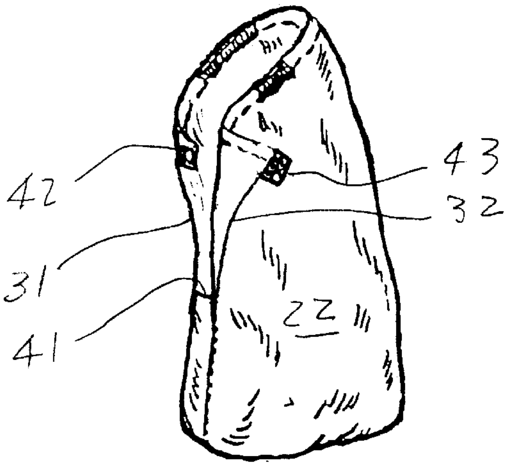
FIG. 6 is a partial, perspective view of an alternative embodiment of the apparatus of the present invention.
Figure 7:
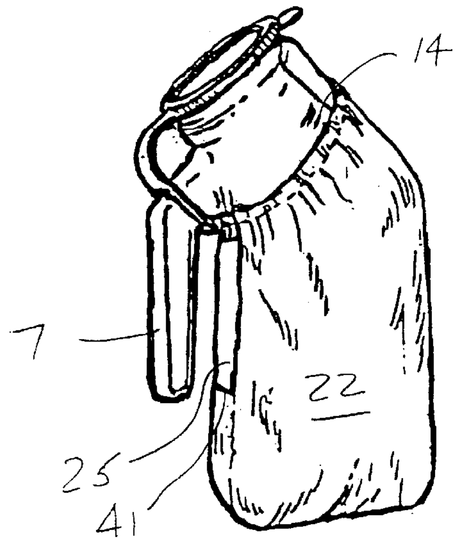
FIG. 7 is another perspective view of the additional alternative embodiment of FIG. 6 illustrating the cover on the receptacle portion of the apparatus of the present invention.

FIGS. 6 and 7 illustrate an alternative embodiment wherein connector panels 42 and 43 are tabs extending from the edges of peripheral panels 31 and 32. In this alternative embodiment, the viewing window 25 may be disposed on the side of cover 22 adjacent handle 7, being a cut-out portion beginning above reference line 41 and extending to connector panels 42 and 43. These alternative features of cover 22 may be utilized together or independently as alternatives to the connector panels 42, 43 and window 25 illustrated in FIGS. 1, 3, 4, and 5.

Figure 8:
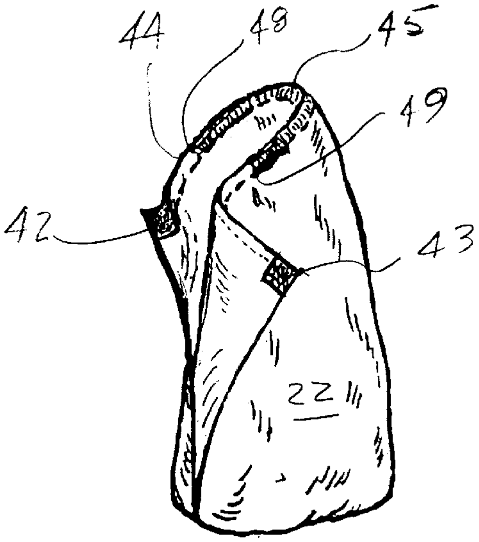
FIG. 8 is a partial, perspective view of an additional alternative embodiment of the apparatus of the present invention.

FIG. 8 illustrates another alternative embodiment wherein elastic band 45 extends less than the entire length of upper panel 44. In the illustrated embodiment, elastic band 45 extends from preselected reference positions 48 and 49 which preferably are disposed approximately at the middle of peripheral panels 36, 37 of side panels 26 and 27, respectively. Depending upon the material of which cover 22 is constructed, a lesser expanse of elastic may provide a more easily assembled cover and vessel 22, 11 while maintaining a snug fit of cover 22 on vessel 11.

| Part No. | Description |
|---|---|
| 10 | urine collection container apparatus |
| 11 | vessel |
| 12 | bottom |
| 13 | side wall |
| 14 | neck |
| 15 | reference line |
| 16 | reference line |
| 17 | handle |
| 18 | joint |
| 19 | cap |
| 20 | strap |
| 21 | bend |
| 22 | cover |
| 23 | bottom panel |
| 24 | large rear panel |
| 25 | window |
| 26 | side panel |
| 27 | side panel |
| 28 | front panel |
| 29 | front panel |
| 30 | stitching |
| 31 | connector panel |
| 32 | connector panel |
| 33 | peripheral panel |
| 34 | peripheral panel |
| 34 | peripheral panel |
| 36 | peripheral panel |
| 37 | peripheral panel |
| 28 | peripheral panel |
| 39 | peripheral panel |

-continued

| Part No. | Description |
|---|---|
| 40 | reference line |
| 41 | reference line |
| 42 | hook connector panel |
| 43 | connector panel |
| 44 | upper panel |
| 45 | elastic bank |
| 46 | fold |
| 47 | fluid level |
| 48 | reference position |
| 48 | reference position |

The foregoing embodiments are presented by way of example only; the scope of the present invention is to be limited only by the following claims.

What is claimed is:

1. A urine collection container and cover apparatus, comprising:

a vessel having an interior, a bottom wall and side walls that define a lower portion of the vessel in a generally rectangular cross-section, a neck defining an upper portion of the vessel which angles away from the longitudinal axis of the vessel, the neck having an opening to the interior of the vessel;

a cover that extends around the vessel below the opening, the cover further comprising at least a bottom panel, a plurality of side panels, a rear panel, a front panel and an upper panel, said side panels, rear panel and front panel disposed in contiguous relation and having a top end and a bottom end generally aligned in extension, said bottom panel extending longitudinally of one of said side panels, rear panel or front panel along its bottom end;

said upper panel of said cover being disposed along the top ends of said side panels, rear panel and front panel, forming a border along the top ends of said panels;

said side panels, rear panel and front panel having a length and width corresponding to the width and length of the sidewalls of said vessel and the bottom panel having a length and width corresponding to the length and width of the bottom wall of said vessel; and said upper panel further comprises a contractible tensible member to hold the cover to the vessel adjacent the neck portion of the vessel.

2. The apparatus of claim 1 wherein said neck is tapered and said upper panel includes a tensible member which constricts to hold said cover to the vessel adjacent the neck portion of the vessel.

3. The apparatus of claim 1 wherein one of said side panels, rear panel, or front panel of said cover includes a longitudinal window for viewing the level of the contents of said vessel.

4. The apparatus of claim 1 wherein the adjacent longitudinal sides of three of said side panels, rear panel and front panel are permanently connected and the remaining longitudinal sides are detachably connected, whereby said cover may be readily removed and replaced over said vessel.

5. The apparatus of claim 4 wherein said remaining longitudinal sides are permanently connected over their lower extent and detachably connected over there upper extent.

6. The apparatus of claim 5 wherein said longitudinal sides are detachably connected with hook and loop fastener material.

7. The apparatus of claim 1 wherein said front panel has first and second longitudinal sections which are detachably connected in a seam to each other and the adjacent longitudinal sides of said side panels, rear panel and front panel are permanently connected.

8. The apparatus of claim 7 wherein a longitudinal window for viewing the contents of said vessel is disposed within the detachably connected seam of said first and second longitudinal sections.

9. The apparatus of claim 7 wherein said first and second longitudinal sections are detachably connected with hook and loop material.

10. The apparatus of claim 7 wherein said first and second longitudinal sections are detachably connected with a zipper.

11. The apparatus of claim 7 wherein said first and second sections are detachably connected with snaps.

12. The apparatus of claim 4 wherein said cover is fabricated of a synthetic material and the permanently connected sides are welded.

13. The apparatus of claim 7 wherein said cover is fabricated of a synthetic material and the permanently connected sides are welded.

14. The apparatus of claim 2 wherein said upper panel includes an elastic member.

* * * * *